United States Patent

Moore et al.

[11] Patent Number: 5,641,684
[45] Date of Patent: Jun. 24, 1997

[54] ION-SENSITIVE DYES

[75] Inventors: Christopher P. Moore, Harrow; Angela King, Bootle; Ian O. Sutherland, West Caldy, all of United Kingdom

[73] Assignee: Johnson & Johnson Clinical Diagnostics, Inc., Rochester, N.Y.

[21] Appl. No.: 493,864

[22] Filed: Jun. 23, 1995

Related U.S. Application Data

[63] Continuation of Ser. No. 104,108, filed as PCT/EP92/02888, Dec. 14, 1992, published as WO93/12428, Jun. 24, 1993, abandoned.

[30] Foreign Application Priority Data

Dec. 18, 1991 [GB] United Kingdom ............... 9126829

[51] Int. Cl.⁶ .................. G01N 33/84; G01N 31/22; C07D 323/00
[52] U.S. Cl. .................. 436/73; 436/74; 436/79; 422/82.06; 422/82.11; 549/348
[58] Field of Search ............. 422/55–61, 82.05, 422/82.06, 82.11; 436/73, 74, 79, 164; 549/348

[56] References Cited

U.S. PATENT DOCUMENTS

| | | | |
|---|---|---|---|
| 4,742,010 | 5/1988 | Lin et al. | 436/74 |
| 5,154,890 | 10/1992 | Mauze et al. | 422/82.07 |
| 5,177,221 | 1/1993 | Cram et al. | 549/348 |
| 5,187,103 | 2/1993 | Czech et al. | 436/79 |

FOREIGN PATENT DOCUMENTS 0287326  10/1988  European Pat. Off. .

OTHER PUBLICATIONS

Alder, J.F. et al. "An Optical Potassium Ion Sensor.", Analyst, Aug. 1987, vol. 112, pp. 1191–1192.

S. Shinkai et al. "Autoaccelerative Diazo Coupling with Calix[4]arene" J. Chem. Society, Perkin Trans. 1, No. 1 1989, 195–196.

E. Nomura et al. "Selective Ion Extraction by a Calix[6] arene Derivative Containing Azo Groups". Chemistry Letters, No. 7, 1989, pp. 1125–1126.

Abstract—T. Shono, "14–Crown–4–Ethers Containing Phenylazo Groups for Metal–Ion Extraction Photometric Reagents and as Ionophores." Chemical Abstracts, vol. 107, No. 20, 16 Nov. 1987.

*Primary Examiner*—David A. Redding

[57] ABSTRACT

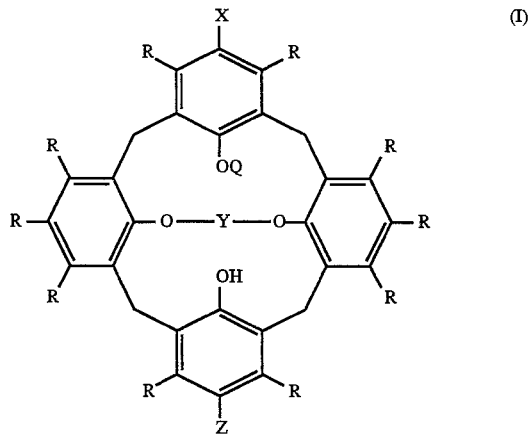

The invention provides compounds represented by formula (I), wherein Y is $-(CH_2)_2[O(CH_2)_2]_n-$ in which n is an integer from 1 to 6; Z is $-N=N-Ar$ in which Ar is a substituted or unsubstituted aryl group; Q is hydrogen or an alkyl group having from 1 to 4 carbon atoms; each R independently is hydrogen or a substituent free of acidic protons; and X is R or Z. The compounds are ion-sensitive dyes suitable for use in optical ion sensors.

9 Claims, 2 Drawing Sheets

ION-SENSITIVE DYES

This is a continuation-in-part of application Ser. No. 08/104,108, filed Aug. 11, 1993 now abandoned, which is the National Stage filing of PCT/EP92/02888, filed Dec. 14, 1992.

The invention relates to compounds which are ion-sensitive dyes. More particularly, the invention relates to dyes which form complexes with cations.

Compounds known as chromoionophores in which an ionophore is directly linked to a chromophore are known. The interaction of such chromoionophores with an ion can result in a colour change. In some cases, the chromoionophore will interact selectively with a particular ion in preference to other ions.

Chromoionophores in which an azo dye chromogenic group is attached to a crown ether ionophore are described in J. F. Alder, D. C. Ashworth, R. Narayanaswamy, R. E. Moss and I. O. Sutherland, Analyst, 1987, 112, 1191. An optical fibre probe utilising such a chromoionophore is reported to respond to potassium ions in aqueous solution with a K$^+$/Na$^+$ selectivity ratio of 6.4.

There is a need for alternative cation-sensitive chromoionophores which give rise to significantly modified visible spectra upon interaction with cations. There is a particular need for such chromoionophores which can interact selectively with cations and which preferably can provide greater selectivity than known chromoionophores.

In a particular application, suitable chromoionophores are required for sensors for the determination of metal ions of physiological importance, for example, the measurement of potassium ions in mammalian blood in the presence of other metal ions. For such an application, the chromoionophore should preferably be highly selective, capable of functioning at physiological pH and capable of responding to the metal ion in the range of concentration in which it is generally present.

The invention provides chromoionophores in the form of ion-sensitive dyes which meet one or more of the above-identified requirements.

The compounds of the invention are represented by the formula

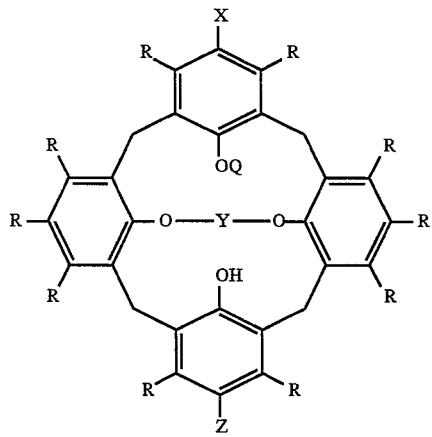

wherein

Y is —(CH$_2$)$_2$[O(CH$_2$)$_2$]$_n$— in which n is an integer from 1 to 6;

Z is —N═N—Ar in which Ar is a substituted or unsubstituted aryl group;

Q is hydrogen or an alkyl group having from 1 to 4 carbon atoms;

each R independently is hydrogen or a substituent free of acidic protons; and,

X is R or Z.

Preferred compounds include those in which n represents 3.

Suitable R substituents include alkyl and alkoxy groups.

The azo dye group Z is preferably a substituted or unsubstituted phenylazo group. Substituents which may be present in the phenyl group include nitro. Specific examples of suitable azo dye groups include 4-nitrophenylazo and 2,4-dinitrophenylazo.

The ion-sensitive dyes of the invention may be employed to sense cations with which they form a complex. The spectral properties of the dyes make them particularly suitable for use in an optical ion sensor. For example, the sensor may be an optical fibre sensor of the type described in the prior art discussed above in which the ion-sensitive compound is immobilised on the tip of the fibre.

The invention provides a method for the determination of a cation in solution comprising contacting a sample of the solution with a sensor comprising an ion-sensitive compound of the invention to form a complex of the cation with the compound and determining the detectable change resulting from the formation of the complex.

The detectable change may be determined by measuring the spectral absorbance characteristics of the ion-sensitive compound.

Figure 1:
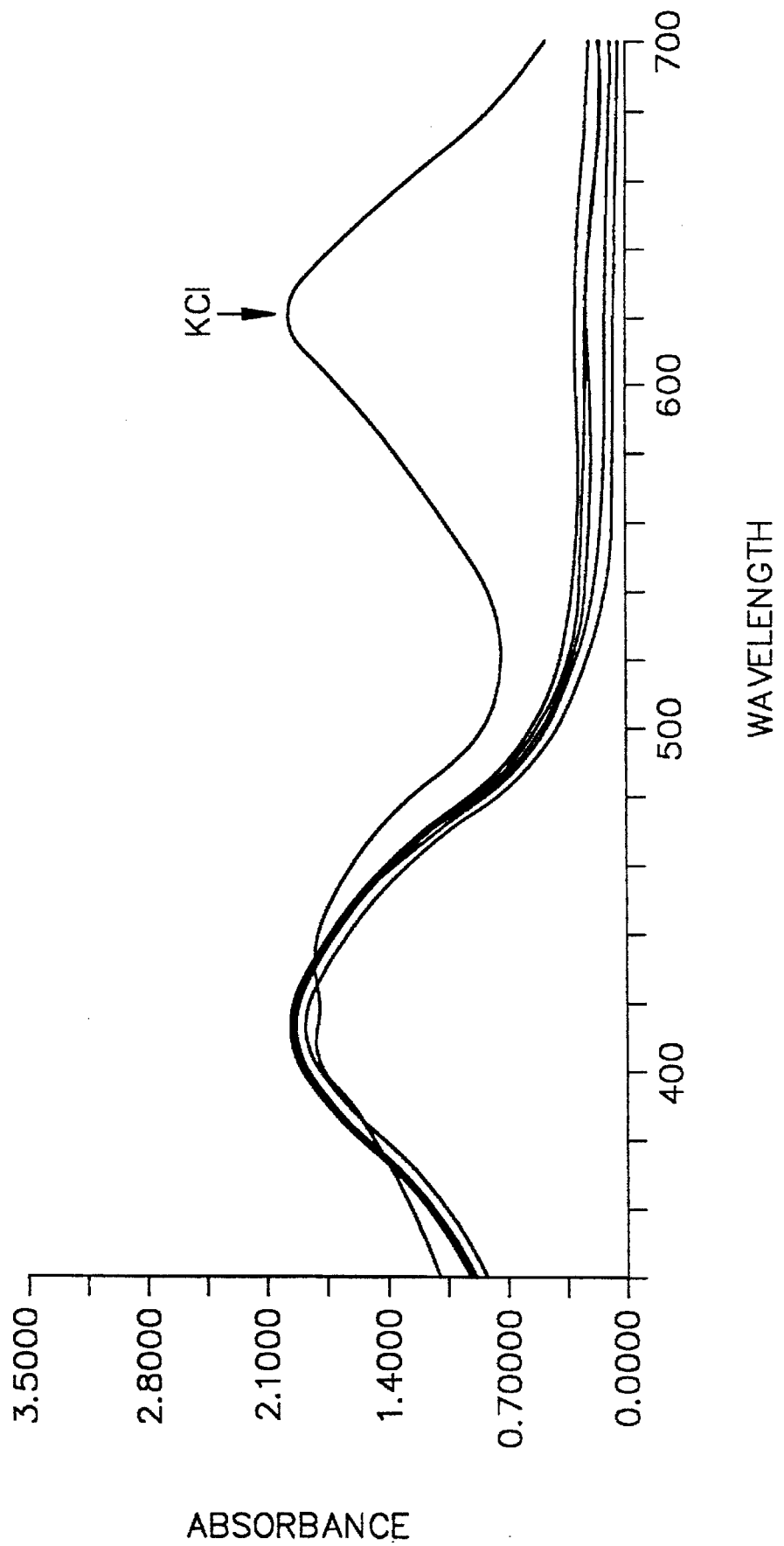
FIGS. 1 and 2 are graphical representations of spectral absorbance data for compounds of the invention.

The compounds of the invention may be prepared by (i) oxidising a bridged calixarene having the formula

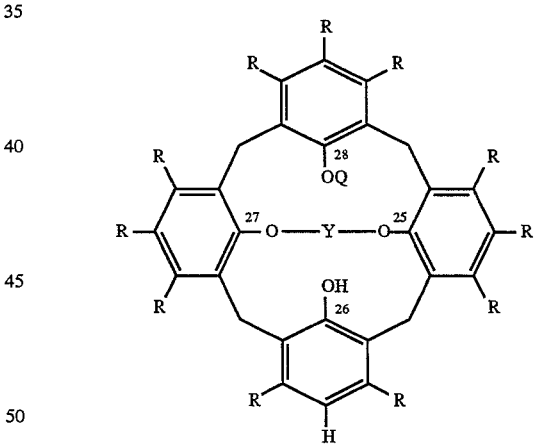

to form the corresponding quinone and (ii) reacting the quinone with an aryl hydrazine of the formula ArNHNH$_2$ under conditions which result in diazo coupling. In the formulae for the bridged calixarene and the aryl hydrazine, Y, Q, R and Ar are as hereinbefore defined.

Bridged calixarene starting materials of the type having the formula shown have been described in the prior art. For example, representative compounds are described in J. Am. Chem. Soc., Vol. 109, No. 15, 1987, 4761–4762.

The oxidation of the bridged calixarene may be performed using thallium trinitrate.

The diazo coupling reaction can be performed in strongly acidic solution, e.g. using concentrated sulphuric acid.

Examples of the preparation and testing of compounds of the invention are as follows.

EXAMPLE 1
The preparation of a mono azo dye is outlined in the following reaction scheme and is described in detail thereafter.
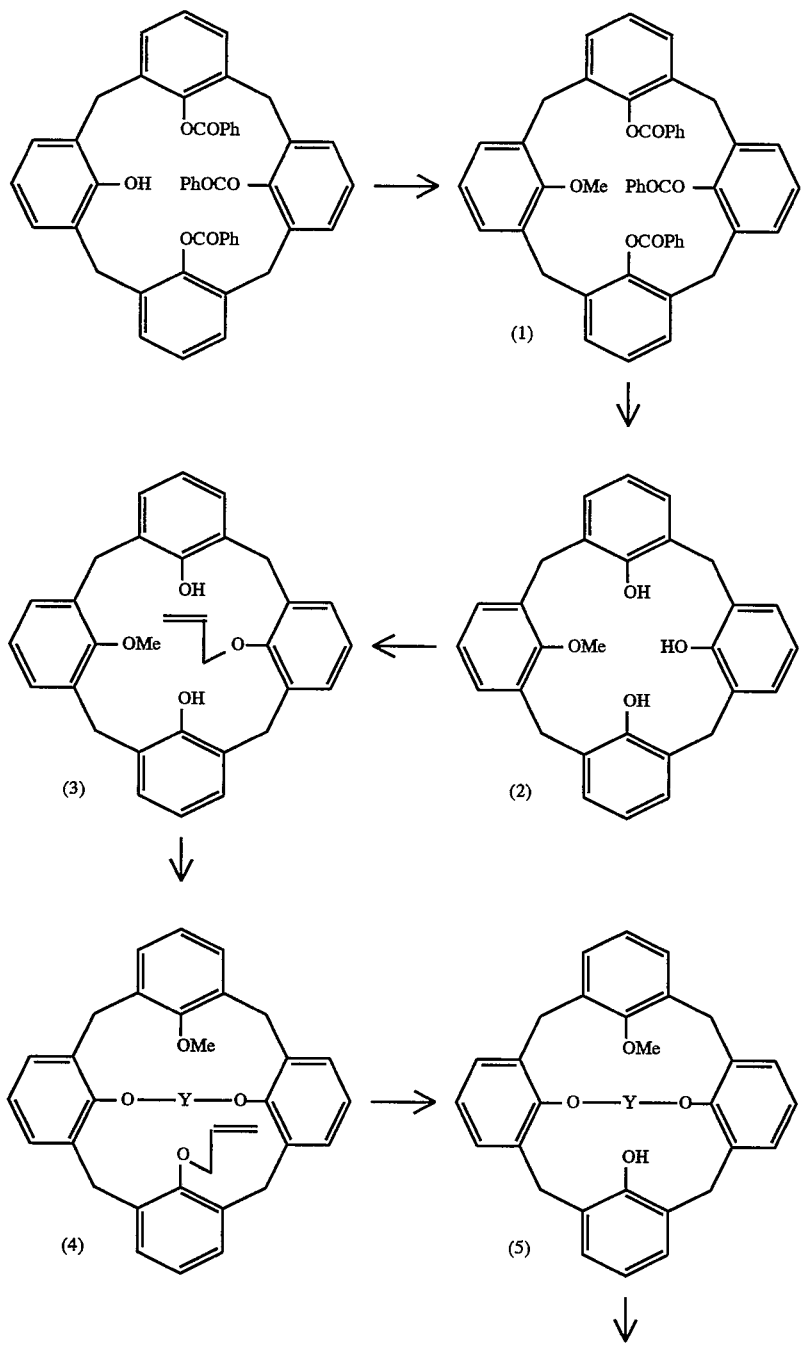

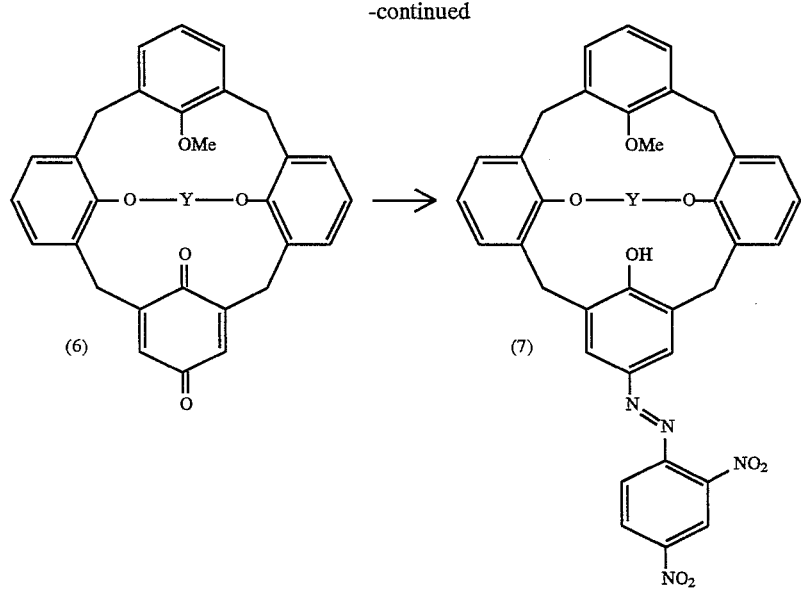

In structures (4)–(7) above, Y represents —(CH$_2$)$_2$[O(CH$_2$)$_2$]$_3$—.

EXPERIMENTAL

25,26,27-Tribenzoyloxy-28-methoxycalix[4]arene (1)

A solution of 25,26,27-tribenzoyloxy-28-hydroxycalix[4]arene (14.72 g, 20 mmol), sodium hydride (1.92 g, 80 mmol, and methyl iodide (7.47 ml, 120 mmol) were refluxed in dry THF (400 ml) overnight. The solvent was removed by evaporation and the compound triturated with methanol and filtered to give a white powder. Recrystallisation from dichloromethane/methanol gave the required compound (11.2 g, 74.6%) as white crystals (m.p. 267°–269° C.)

δH(CDCl$_3$) 8.02–7.13 (m,16,ArH), 6.89–6.43 (m,11, ArH), 3.97–3.34 (m,8H,ArCH$_2$Ar), 3.65 (s,3,OCH$_3$)

Found: C,76.95; H,4.77 (C$_{50}$H$_{38}$O$_7$.½CH$_2$Cl$_2$ requires C, 77.21; H, 5.08)

M$^+$ found: 750.261 (C$_{50}$H$_{38}$O$_7$ requires 750.262).

25,26,27-trihydroxy-28-methoxycalix[4]arene (2)

A solution containing 25,26,27-tribenzoyloxy-28-methoxycalix[4]arene (11.2 g, 15 mmol) in THF (400 ml) was treated with a solution of sodium hydroxide (35.8 g) in water (120 ml) and ethanol (280 ml), and the mixture refluxed for 18 hrs. The solvent was removed by evaporation, the residue was treated with dilute hydrochloric acid and the organic material was extracted into CH$_2$Cl$_2$. Evaporation of the solvent gave the crude product which was purified by column chromatography (silica, 50/50 petroleum ether (60/80) chloroform) and recrystallisation from chloroform/methanol gave the product as white crystals (5.62 g, 85.9%), m.p. 249°–250° C.

δ(CDCl$_3$) 9.67 (s,1,ArOH), 9.31 (s,2,ArOH), 7.14–6.80 (m,9,ArH), 6.67 (t,3,ArH), 4.31 (pair d, 4,ArCH$_2$Ar), 4.07 (s,3,OCH$_3$), 3.45 (d,4,ArCH$_2$Ar).

Found: C,79.47; H,5.94 (C$_{29}$H$_{26}$O$_4$ requires C,79.43; H,5.98)

M.S. M/e 438 (M$^+$) 100%

M$^+$ found 438.183 (C$_{29}$H$_{26}$O$_4$ requires 438.183).

25,27-dihydroxy-26-allyloxy-28-methoxycalix[4]arene (3)

The calixarene (2) (0.85 g, 1.94 mmol) and anhydrous potassium carbonate (0.88 g, 6.38 mmol) were mixed in dimethyl ketone and the reaction mixture heated under reflux for one hour. Allyl bromide (0.24 g, 1.9 mmol) was added and the reaction mixture heated under reflux overnight. The reaction was cooled, the solvent evaporated and the residue partitioned between water (50 ml) and dichloromethane (100 ml). The aqueous layer was further extracted with dichloromethane (2×50 ml). The combined extracts were dried (MgSO$_4$) and the solvent evaporated to leave the product (0.65 g, 70%) which was purified by column chromatography (silica, chloroform) to give a white solid m.p. 164° C.

δ(CDCl$_3$) 6.96–6.37 (m,12,ArH), 6.07(m,1, C—CH=C), 5.50 (d,2H, C=CH$_2$), 5.22 (d, 2H, C=CH$_2$), 4.40 (d,2H, OCH$_2$C=C), 4.17 (d,4,ArCH$_2$Ar), 3.65 (s,3,OCH$_3$), 3.24 (d,4,ArCH$_2$Ar)

M.S. m/e 478 (M$^+$) 100%

M$^+$ found: 478.214 (C$_{32}$H$_{30}$O$_4$ requires 478.214).

25,27-(13-crown-5)-26-allyloxy-28-methoxycalix[4]arene (4)

The calixarene (3) (0.5 g, 1.04 mmol) was dissolved in dry toluene (50 ml) and the solution added dropwise to a vigorously stirred suspension of tetraethylene glycol ditosylate (0.52 g, 1.05 mmol) and $^t$BuOK (0.26 g, 2.3 mmol) in dry toluene (50 ml) that was heated under reflux. After the addition was complete the reaction mixture was refluxed overnight and then cooled and quenched with water. The toluene was evaporated and the residue partioned between water (20 ml) and dichloromethane (30 ml). The aqueous layer was extracted with two further portions of dichloromethane and the combined extracts dried (MgSO$_4$) and the solvent evaporated. Purification was carried out using K$^+$ loaded column chromatography to give a white solid m.p. 127° C.

δ(CDCl$_3$) 7.17–6.56(m,12,ArH), 6.50–5.87(m,3, CH=CH$_2$), 4.40 (m,4,ArCH$_2$Ar), 4.24–3.33 (m,18,OCH$_2$), 4.12 (s,3,OCH$_3$), 3.13 (m,4,ArCH$_2$Ar)

M$^+$ found: 636.310 (C$_{40}$H$_{44}$O$_7$ requires 636.309).

25,27-(13-crown-5)-26-hydroxy-28-methoxycalix[4]arene

A mixture of the calixarene (4) (70 mg, 0.11 mmol), 10% palladium/carbon (120 mg, 0.11 mmol) and p-toluenesulphonic acid (42 mg, 0.22 mmol) were stirred in ethanol (40 ml), containing dichloromethane (5 ml) under argon for four days. Sodium carbonate (0.1 g) was added and the mixture filtered through celite, the celite was then washed with ethanol and then dichloromethane. The solvents were evaporated in vacuo and the compound redissolved in dichloromethane, washed with water several times and dried (MgSO$_4$). The crude product was significantly purified using cation loaded column chromatography (silica/ 10%KBr, dichloromethane up to dichloromethane 3% ethanol, then washed with ethanol). The solvents were evaporated and the compound redissolved in dichloromethane (50 ml) and washed with HCl (3M, aqueous solution) and water and evaporated to give the product (0.038 g, 57.9%) m.p. 188°–198° C.

$\delta$(CDCl$_3$) 7.72 (s,1,ArOH), 7.20–6.87 (m,7,ArH), 6.80 (d,2,ArH), 6.74–6.54 (m,3,ArH), 4.37 (m,4,ArCH$_2$Ar) 4.27–3.51 (m,19,OCH$_2$, OCH$_3$), 3.34 (m,4,ArCH$_2$Ar)

M.S. m/e 596 M$^+$ (100%)

M$^+$ found: 596.277 (C$_{37}$H$_{40}$O$_7$ requires 596.277).

Mono-quinone (6)

Thallium trinitrate (76 mg, 0.17 mmol) was dissolved in methanol (24 ml) and then ethanol (60 ml) added. A solution of the calixarene (5) (34 mg, 0.05 mmol) in chloroform (24 ml) was then added, and the resulting yellow solution stirred for ten minutes. On addition of water (60 ml) a dark brown mixture resulted which was stirred for a further 25 minutes. The layers were separated and the organic layer washed with water. The solution was evaporated in vacuo and the crude material purified by column chromatography (silica, 3% EtOH:CH$_2$Cl$_2$) to give a yellow compound (65 mg, 83.5%) m.p. 164° C.

$\delta$(CDCl$_3$) 7.22–6.28 (m,9,ArH), 6.07 (s,2, quinone H), 4.31–3.1 (m,27,ArCH$_2$Ar,OCH$_2$,OCH$_3$).

Mono-2,4-dinitroazophenol dye (7)

To a yellow solution of the quinone (50 mg, 0.08 mmol) in chloroform (10 ml) was added ethanol (12 ml). A solution of 2,4-dinitrophenylhydrazine (5.0 g, 25.2 mmol) and concentrated sulphuric acid (10 ml) in ethanol (75 ml) was prepared. A portion of this (1.2 ml, 0.4 mmol) was added to the solution to give a red solution which was stirred for 1 hour. The solution was evaporated in vacuo and dichloromethane (20 ml) added and the solution washed with water and evaporated. The residue was partially purified by prep. chromatography (tlc), the major band was extracted with dichloromethane/methanol. The solvents were evaporated and dichloromethane added (20 ml). The solution was washed with HCl (3M, aqueous solution) and water, and evaporated to give the pure mono-azo phenol as dark red crystals (40 mg, 62%) m.p. 102° C.

$\delta$(CDCl$_3$, major conformer) ABC system, $\delta_A$ 8.77, $\delta_B$ 8.50, $\delta_C$ 7.88 (J$_{AB}$ 2.4, J$_{BC}$ 8.8 Hz, H-3', H-5' and H-6'), 8.32 (s, OH), 7.82 (s, 2 aryl-H), A$_2$B system, $\delta_A$ 7.18, $\delta_B$ 6.96 (J$_{AB}$ 7.2 Hz, 3 aryl-H), ABC system, $\delta_A$ 6.71, $\delta_B$ 6.65, $\delta_C$ 6.57 (J$_{AB}$1.2, J$_{AC}$ 7.6, J$_{BC}$ 7.6 Hz, 2x3 aryl-H), AB system, $\delta_A$ 4.60, $\delta_B$ 3.46 (J$_{AB}$ 13.6 Hz, 2xArCH$_2$Ar), AB system, $\delta_A$ 4.36, $\delta_B$ 3.28 (J$_{AB}$ 12.8 Hz, 2xArCH$_2$Ar), 4.09 (s, OMe), and 3.7–4.2 (m, 4xOCH$_2$CH$_2$O)

$\delta$(CDCl$_3$, minor conformer) ABC system, $\delta_A$ 8.78, $\delta_B$ 8.50, $\delta_C$ 7.85 (J$_{AB}$ 2.4, J$_{BC}$ 8.8 Hz, H-3', H-5' and H-6'), 8.26 (s, OH), 7.79 (s, 2 aryl-H), A$_2$B system, $\delta_A$ 7.27, $\delta_B$ 7.05 (J$_{AB}$ ca 8 Hz, 3 aryl-H), ABC system, $\delta_A$ 7.04, $\delta_B$ 6.91, $\delta_C$ 6.79 (J$_{AB}$ ca 1, J$_{AC}$ 7.4, J$_{BC}$ 7.4 Hz 2x3 aryl-H), AB system, $\delta_A$ 4.42, $\delta_B$ 3.37 (J$_{AB}$ 13.4 Hz, 2xArCH$_2$Ar).

m/z 790 (M$^+$) 791 (M+1)$^+$, 813 (M+Na)$^+$ and 829 (M+K)$^+$.

Found: C, 65.6; H, 5.3; N, 7.0%. C$_{43}$H$_{42}$N$_4$O$_{11}$ requires C, 65.3; H, 5.3; N, 7.1%.

SOLUTION EXPERIMENTS

The spectral absorbance characteristics of a 1M solution of the mono-azo dye (7) at pH8 were measured. As shown by the spectral data given in FIG. 1, the mono-azo dye shows a modified spectrum in solution when potassium ions are present. Similar modified spectra are not obtained in the presence of other group IA cations such as lithium, sodium, rubidium and caesium as shown in FIG. 1. Group IIA cations magnesium and calcium gave no response.

In conclusion, the mono-azo dye is a chromoionophore which is highly selective for potassium ions. A K$^+$/Na$^+$ discrimination of ca 1000:1 has been demonstrated.

EXAMPLE 2

Mono-4-nitroazophenol dye

In a manner analogous to the preparation of dye (7), a mono-4-nitroazophenol dye was prepared by reacting the quinone (6) with 4-nitrophenylhydrazine.

In solution experiments as described above the mono-4-nitroazophenol dye gave similar results to those achieved for the dye (7) with regard to sensitivity and selectivity.

EXAMPLE 3

The preparation of a bis-azo dye is represented by the following reaction scheme

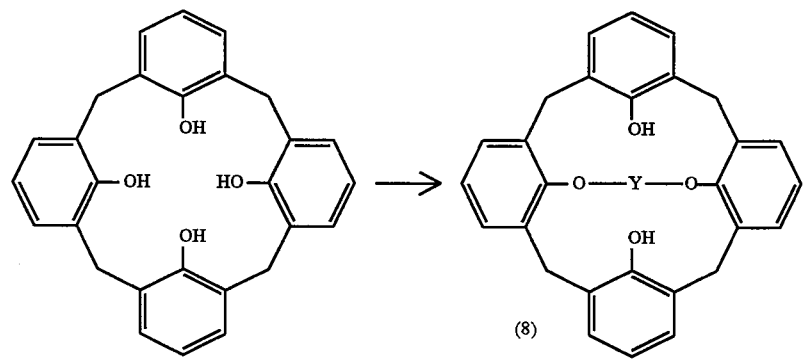

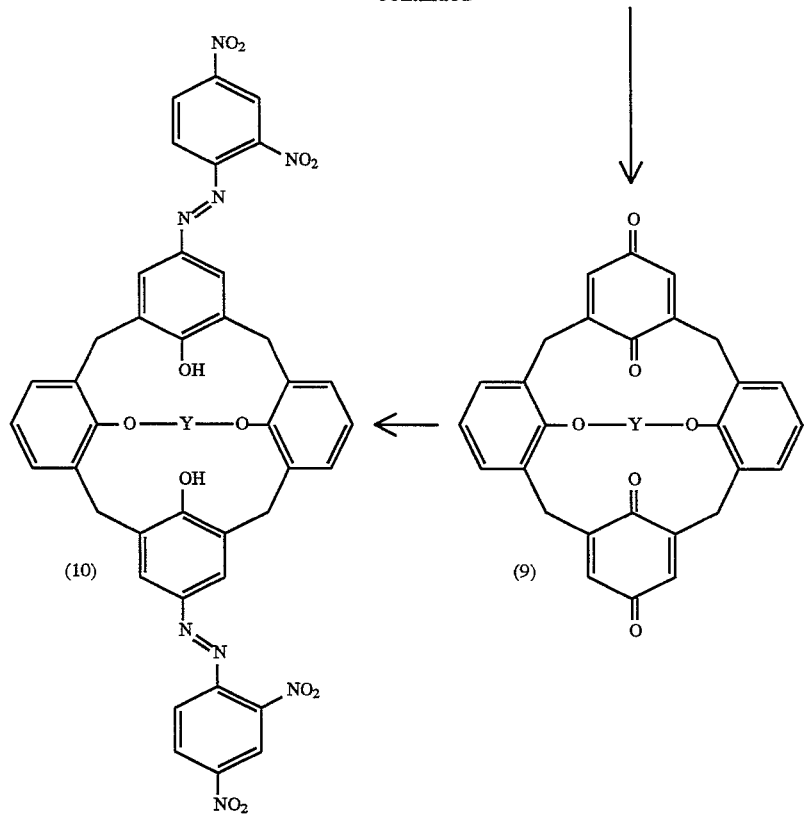

In structures (8) to (10) above, Y represents —(CH$_2$)$_2$[O(CH$_2$)$_2$]$_3$—.

EXPERIMENTAL

25,27-dihydroxy-26,28-(13-crown-5)-calix[4]arene (8)

25,26,27,28-Tetrahydroxycalix[4]arene (8.48 g, 20 mmol) was dissolved in dry toluene (150 ml) and the solution added dropwise over 2 hrs to a vigorously stirred suspension of tetraethylene glycol ditosylate (10.04 g, 20 mmol) and ᵗBuOK (8.98 g, 80 mmol) in dry toluene (150 ml) that was heated under reflux. After the addition was complete the reaction mixture was gently refluxed overnight and then cooled. The toluene was evaporated and the residue partitioned between water (200 ml) and dichloromethane (400 ml). The aqueous layer was extracted with two further portions of CH$_2$Cl$_2$ and the combined extracts dried (MgSO$_4$) and the solvent evaporated. The crude product was purified by column chromatography (silica, 5%EtOH:CH$_2$Cl$_2$) followed by recrystallisation from dichloromethane/methanol to give the product (5.23 g, 45%) as white crystals, m.p., 273°–275° C.;

$\delta$(CDCl$_3$): 7.07 (d,4H,ArH), 6.84 (d,4H,ArH), 6.68 (m,4H,ArH), 4.41 (d,4H,ArCH$_2$Ar), 4.07 (s,8H,OCH$_2$), 3.93 (M,4H,OCH$_2$), 3.85 (m,4H,OCH$_2$), 3.34 (d,4H,ArCH$_2$Ar), Found: C,73.96; H,6.32 (C$_{36}$H$_{38}$O$_7$ requires C, 74.21; H, 6.57)

M.S.: m/e 582 (M$^+$) (100%).

Bis-quinone (9)

Thallium trinitrate (2.29 g, 5.16 mmol) was dissolved in methanol (400 ml) and then ethanol added (1000 ml). A solution of the calixarene (8) (0.5 g, 0.86 mmol) in chloroform (400 ml) was then added, and the resulting yellow solution stirred for ten minutes. On addition of water (1000 ml) a dark brown mixture resulted which was stirred for a further 15 minutes. The layers were separated and the organic layer washed with water. The solution was evaporated in vacuo and the crude material purified by column chromatography (silica 5%EtOH;CH$_2$Cl$_2$) to give the quinone (0.36 g, 67%) as a yellow powder.

$\delta$(CDCl$_3$) 6.89(d,4H,ArH), 6.75(m,2H, ArH), 6.66 (s,4H, quinone), 3.85 (s,8H,ArCH$_2$Ar), 3.90–3.25 (m,16H, OCH$_2$)

Found: C,71.02; H,6.09 (C$_{36}$H$_{34}$O$_9$ requires C,70.81; H.5.61).

Bis-2,4-dinitrophenylazo dye (10)

To a yellow solution of the bis-quinone (9) (0.2 g, 0.33 mmol) in chloroform (40 ml) was added 50 ml of ethanol. A solution of 2,4-dinitrophenylhydrazine (5.0 g, 25.2 mmol) and concentrated sulphuric acid (10 ml) in ethanol (75 ml) was prepared. A portion of this solution (4.9 ml, 1.6 mmol) was added to the quinone solution to give a red solution, which was stirred for 1 hour. The solution was evaporated in vacuo and dichloromethane (50 ml) was added and the solution washed with water and evaporated. The residue was purified by preparative chromatography (tlc), the major band was extracted with dichloromethane/methanol. The solvents were evaporated and dichloromethane (50 ml) was added, the solution was washed with HCl (3M, aqueous solution) and water and evaporated to give the bis (azophenol) as an orange solid (0.16 g, 50.3%) mp 275°–277° C.

$\delta$(CDCl$_3$) 8.69(m,ArH,2H), 8.53(m,ArH,2H), 8.26 (m,ArH,2H, 7.57 (s,ArH,4H), 6.73 (d,ArH,4H), 6.55 (m,ArH,2H), 4.27 (d,ArCH$_2$Ar4H), 4.01–3.42 (m, OCH$_2$CH$_2$O,16H), 3.29 (d,ArCH$_2$Ar,4H)

Found: C,60.19; H,5.09; N,12.17 ($C_{48}H_{42}N_8O_5$ requires C,59.38; H,4.36; N,11.54).

SOLUTION EXPERIMENTS

Figure 2:
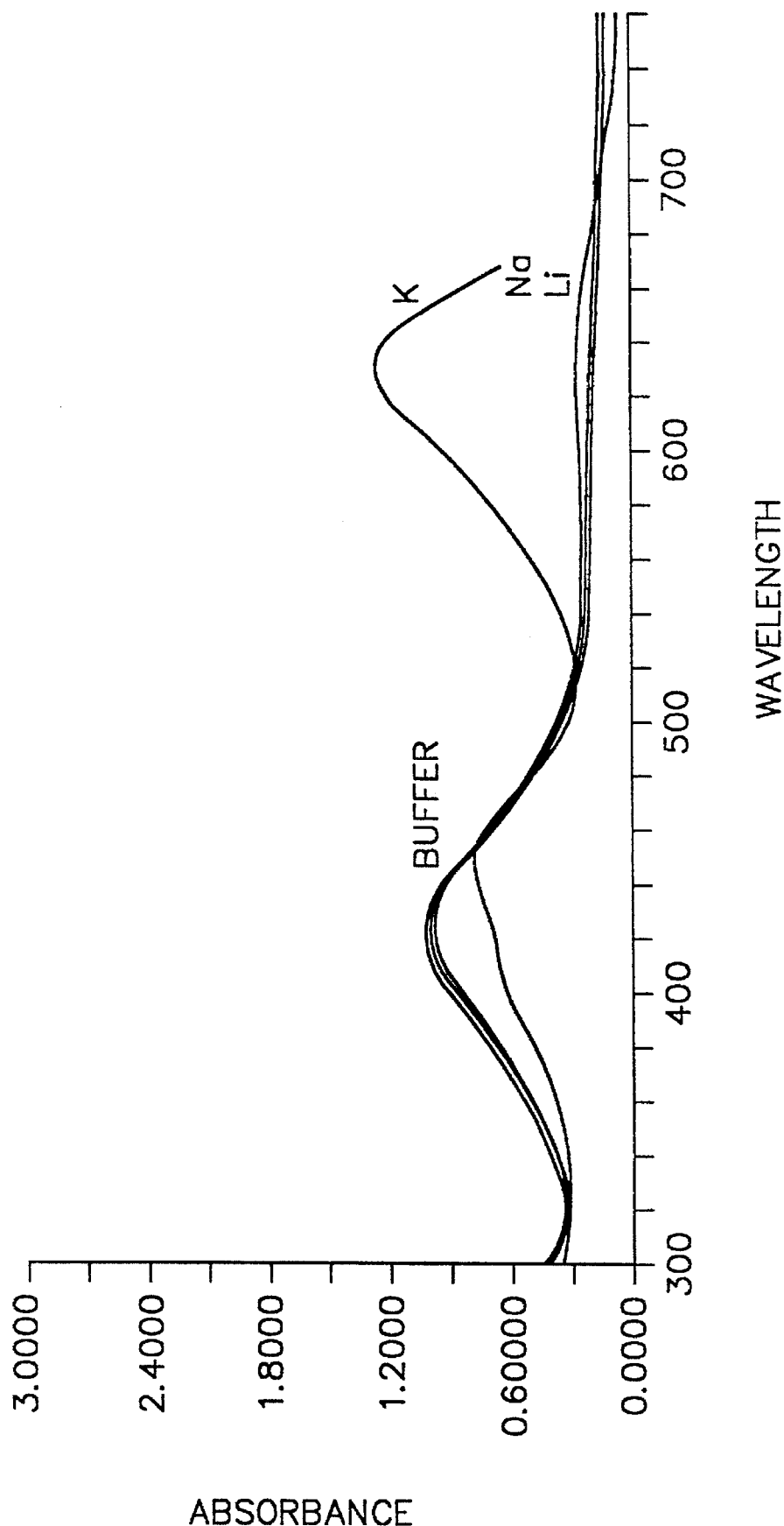

The spectral absorbance characteristics of a 1M solution of the bis-azo dye (10) at pH8 were measured. As shown by the spectral data presented in FIG. 2, the bis-azo dye gives similar results to the mono azo dye of Example 1 for Group IA cations i.e. a high selectivity for potassium ions is demonstrated. In addition, the bis-azo dye shows some sensitivity to Group IIA cations, particularly strontium ions and, to a lesser extent, calcium ions.

We claim:

1. A compound represented by the formula

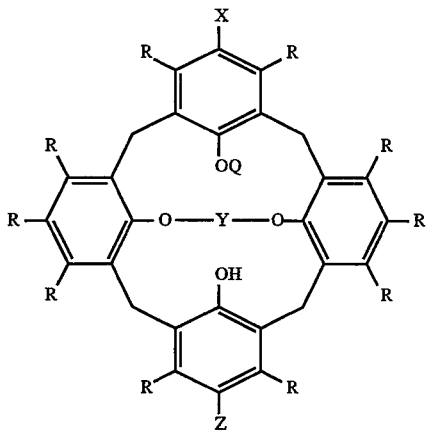

wherein

Y is —$(CH_2)_2[O(CH_2)_2]_n$— in which n is an integer from 1 to 6;

Z is —N═N—Ar in which Ar is a substituted or unsubstituted aryl group;

Q is hydrogen or an alkyl group having from 1 to 4 carbon atoms;

each R independently is hydrogen or a substituent free of acidic protons; and,

X is R or Z.

2. A compound according to claim 1 wherein n is 3.

3. A compound according to claim 1 wherein each R independently is hydrogen.

4. A compound according to claim 1 wherein Z is a substituted or unsubstituted phenylazo group.

5. A compound according to claim 4 wherein each Z independently is a 4-nitrophenylazo or a 2,4-dinitrophenylazo group.

6. An optical ion sensor comprising a sensor member and an ion-sensitive compound associated therwith wherein the compound is a compound according to claim 1.

7. A sensor according to claim 6 wherein the sensor member comprises an optical fibre having a tip and the compound is immobilised on the tip of the optical fibre.

8. A method for the determination of a cation in solution comprising contacting a sample of the solution with a sensor member containing an ion-sensitive compound to form a complex of the cation with the compound and determining the detectable change resulting from the formation of the complex.

9. The method of claim 8, wherein the sensor member is an optical fibre and the compound is immobilised on the tip of the optical fibre.

* * * * *